US011083916B2

(12) United States Patent
Duffy et al.

(10) Patent No.: US 11,083,916 B2
(45) Date of Patent: Aug. 10, 2021

(54) FLAT FOLD RESPIRATOR HAVING FLANGES DISPOSED ON THE MASK BODY

(75) Inventors: Dean R. Duffy, Woodbury, MN (US); Scott A. Spoo, Deer Park, WI (US); Thomas I. Insley, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1514 days.

(21) Appl. No.: 12/338,084

(22) Filed: Dec. 18, 2008

(65) Prior Publication Data

US 2010/0154805 A1 Jun. 24, 2010

(51) Int. Cl.
*A61B 19/00* (2006.01)
*A62B 23/02* (2006.01)
*A41D 13/11* (2006.01)

(52) U.S. Cl.
CPC ........ *A62B 23/025* (2013.01); *A41D 13/1115* (2013.01)

(58) Field of Classification Search
CPC .. A62B 23/025; A41D 13/11; A41D 13/1161; A41D 13/1115; A41D 13/1123
USPC .... 128/863, 206.13, 206.12, 206.19, 206.21, 128/206.27, 206.28, 857
See application file for complete search history.

(56) References Cited

U.S. PATENT DOCUMENTS 2,227,667 A * 1/1941 Panettiere .......... A41D 13/1146 128/863
3,500,825 A * 3/1970 Erik ...................... A41D 13/11 128/206.19
3,971,369 A 7/1976 Aspelin et al.
3,971,373 A 7/1976 Braun
3,985,132 A 10/1976 Boyce et al.
4,013,816 A 3/1977 Sabee
4,215,682 A 8/1980 Kubik
4,248,220 A 2/1981 White
4,269,315 A 5/1981 Boyce
4,300,549 A 11/1981 Parker
RE31,285 E 6/1983 Van Turnhout
4,419,994 A 12/1983 Hilton
(Continued)

FOREIGN PATENT DOCUMENTS

CA 1296487 3/1992
EP 894443 2/1999
(Continued)

OTHER PUBLICATIONS

Search Report from International Application No. PCT/US2009/063691 dated May 28, 2010.
(Continued)

*Primary Examiner* — Victoria J Hicks

(57) ABSTRACT

A flat-fold, filtering, face-piece respirator 10 that has a harness 14, a mask body 12, and first and second flanges 30*a*, 30*b*. The mask body 12 is capable of being folded flat for storage and can be opened into a cup-shaped configuration for use. The mask body 12 includes a filtering structure 16 and has the first and second flanges 30*a*, 30*b* disposed on first and second mask body sides. The first and second flanges 30*a*, 30*b* project both laterally x and frontally y from the mask body 12. The provision of the flanges on each side of the respirator is beneficial to ease of mask donning, doffing, and adjustment, and to face fit and maintaining the open shape or configuration of the mask body.

22 Claims, 3 Drawing Sheets

(56) References Cited

U.S. PATENT DOCUMENTS

| | | | | |
|---|---|---|---|---|
| 4,536,440 | A | 8/1985 | Berg | |
| 4,550,856 | A | 11/1985 | Ballmann | |
| 4,588,537 | A | 5/1986 | Klaase | |
| 4,600,002 | A | 7/1986 | Maryyanek | |
| 4,673,084 | A | 6/1987 | Hubbard | |
| 4,688,566 | A | 8/1987 | Boyce | |
| 4,722,857 | A | 2/1988 | Tomioka et al. | |
| 4,790,306 | A | 12/1988 | Braun | |
| 4,798,850 | A | 1/1989 | Brown | |
| 4,807,619 | A | 2/1989 | Dyrud | |
| 4,966,140 | A * | 10/1990 | Herzberg | A41D 13/1115 128/206.12 |
| 5,237,986 | A | 8/1993 | Seppala | |
| 5,322,061 | A | 6/1994 | Brunson | |
| 5,325,892 | A | 7/1994 | Japuntich | |
| 5,336,552 | A | 8/1994 | Strack et al. | |
| 5,496,507 | A | 3/1996 | Angadjivand | |
| 5,529,056 | A * | 6/1996 | Brunson et al. | 128/200.24 |
| 5,553,608 | A * | 9/1996 | Reese | A41D 13/1115 128/206.19 |
| 5,558,089 | A | 9/1996 | Castiglione | |
| 5,615,767 | A | 4/1997 | Eull | |
| 5,617,849 | A | 4/1997 | Springett | |
| 5,656,368 | A | 8/1997 | Braun | |
| 5,701,893 | A | 12/1997 | Kern | |
| 5,803,077 | A | 9/1998 | Gazzara | |
| 5,804,295 | A | 9/1998 | Braun | |
| 5,908,598 | A | 6/1999 | Rousseau | |
| 5,927,280 | A | 7/1999 | Miyake | |
| D412,573 | S | 8/1999 | Castiglione | |
| 6,041,782 | A | 3/2000 | Angadjivand | |
| 6,062,221 | A | 5/2000 | Brostrom | |
| 6,123,077 | A | 9/2000 | Bostock | |
| 6,234,171 | B1 | 5/2001 | Springett | |
| 6,332,465 | B1 | 12/2001 | Xue | |
| 6,334,671 | B1 | 1/2002 | Umehara | |
| 6,336,459 | B1 | 1/2002 | Miyake | |
| 6,375,886 | B1 | 4/2002 | Angadjivand | |
| 6,391,429 | B1 | 5/2002 | Senkus | |
| 6,394,090 | B1 | 5/2002 | Chen et al. | |
| 6,397,458 | B1 | 6/2002 | Jones | |
| 6,398,847 | B1 | 6/2002 | Jones | |
| 6,406,657 | B1 | 6/2002 | Eitzman | |
| 6,409,806 | B1 | 6/2002 | Jones | |
| 6,454,986 | B1 | 9/2002 | Eitzman | |
| 6,484,722 | B2 | 11/2002 | Bostock et al. | |
| 6,492,286 | B1 | 12/2002 | Berrigan | |
| RE37,974 | E | 2/2003 | Bowers | |
| 6,568,392 | B1 | 5/2003 | Bostock et al. | |
| 6,743,464 | B1 | 6/2004 | Insley | |
| 6,763,970 | B2 | 7/2004 | Harris | |
| 6,783,574 | B1 | 8/2004 | Angadjivand | |
| 6,824,718 | B2 | 11/2004 | Eitzman | |
| 6,843,248 | B2 | 1/2005 | Japuntich | |
| 6,854,463 | B2 | 2/2005 | Japuntich | |
| 6,868,984 | B2 | 3/2005 | Griesbach | |
| 6,883,518 | B2 | 4/2005 | Mittelstadt | |
| 6,886,563 | B2 * | 5/2005 | Bostock et al. | 128/206.19 |
| 6,923,182 | B2 | 8/2005 | Angadjivand | |
| 7,013,895 | B2 | 3/2006 | Martin | |
| 7,028,689 | B2 | 4/2006 | Martin | |
| 7,036,507 | B2 | 5/2006 | Jensen | |
| 7,086,401 | B2 | 8/2006 | Chiam | |
| 7,117,868 | B1 | 10/2006 | Japuntich | |
| 7,131,442 | B1 | 11/2006 | Kronzer | |
| RE39,493 | E | 2/2007 | Yuschak | |
| 7,188,622 | B2 | 3/2007 | Martin | |
| 7,311,104 | B2 | 12/2007 | Japuntich | |
| 7,428,903 | B1 | 9/2008 | Japuntich | |
| 7,677,248 | B2 * | 3/2010 | Gerson | A41D 13/1123 128/205.25 |
| 7,766,015 | B2 | 8/2010 | Harold | |
| 8,066,006 | B2 | 11/2011 | Daugaard | |
| D659,821 | S | 5/2012 | Spoo | |
| 2005/0098182 | A1 | 5/2005 | Callan | |
| 2006/0283454 | A1 | 12/2006 | Delaney et al. | |
| 2007/0044803 | A1 | 3/2007 | Xue | |
| 2007/0068529 | A1 | 3/2007 | Kalatoor | |
| 2007/0157932 | A1 | 7/2007 | Cerbini | |
| 2007/0210096 | A1 | 9/2007 | Ellswood | |
| 2008/0011308 | A1 | 1/2008 | Fleming | |
| 2008/0105261 | A1 | 5/2008 | Harold et al. | |
| 2008/0271737 | A1 | 11/2008 | Facer | |
| 2010/0154805 | A1 | 6/2010 | Duffy | |
| 2010/0154806 | A1 | 6/2010 | Duffy | |
| 2011/0067700 | A1 | 3/2011 | Spoo | |
| 2011/0315144 | A1 | 12/2011 | Eitzman | |
| 2012/0097167 | A1 | 4/2012 | Ono | |

FOREIGN PATENT DOCUMENTS

| | | | | |
|---|---|---|---|---|
| EP | 1495785 | | 1/2005 | |
| EP | 737316 | | 1/2007 | |
| FR | 2908050 | | 5/2008 | |
| FR | 2908050 | A1 * | 5/2008 | A41D 13/1123 |
| GB | 2045093 | | 10/1980 | |
| GB | 2103491 | | 2/1983 | |
| JP | 05-044147 | | 6/1993 | |
| JP | 06-335535 | | 12/1994 | |
| JP | 2003-093528 | | 4/2003 | |
| JP | 2005-348998 | | 12/2005 | |
| JP | 3125147 | | 9/2006 | |
| JP | 03138154 | | 11/2007 | |
| KR | 20-2008-0004833 | | 10/2008 | |
| KR | 2008-0102881 | | 11/2008 | |
| KR | 10-0996678 | | 11/2010 | |
| WO | WO 1996-28216 | | 9/1996 | |
| WO | WO 99/06116 | | 2/1999 | |

OTHER PUBLICATIONS

European Application 09837769 Search Report dated Jun. 4, 2015.

U.S. Appl. No. 13/727,923, Office Action dated Feb. 26, 2015, 33 pages.

U.S. Appl. No. 13/728,008, Office Action dated Sep. 10, 2014, 14 pages.

* cited by examiner

FLAT FOLD RESPIRATOR HAVING FLANGES DISPOSED ON THE MASK BODY

The present invention pertains to a flat fold respirator that has first and second flanges provided on each side of the mask body.

BACKGROUND

Respirators are commonly worn over the breathing passages of a person for at least one of two common purposes: (1) to prevent impurities or contaminants from entering the wearer's breathing track; and (2) to protect other persons or things from being exposed to pathogens and other contaminants exhaled by the wearer. In the first situation, the respirator is worn in an environment where the air contains particles that are harmful to the wearer, for example, in an auto body shop. In the second situation, the respirator is worn in an environment where there is risk of contamination to other persons or things, for example, in an operating room or clean room.

A variety of respirators have been designed to meet either (or both) of these purposes. Some respirators have been categorized as being "filtering face-pieces" because the mask body itself functions as the filtering mechanism. Unlike respirators that use rubber or elastomeric mask bodies in conjunction with attachable filter cartridges (see, e.g., U.S. Patent RE39,493 to Yuschak et al.) or insert-molded filter elements (see, e.g., U.S. Pat. No. 4,790,306 to Braun), filtering face-piece respirators are designed to have the filter media cover much of the whole mask body so that there is no need for installing or replacing a filter cartridge. These filtering face-piece respirators commonly come in one of two configurations: molded respirators and flat-fold respirators.

Molded filtering face piece respirators have regularly comprised non-woven webs of thermally-bonding fibers or open-work plastic meshes to furnish the mask body with its cup-shaped configuration. Molded respirators tend to maintain the same shape during both use and storage. These respirators therefore cannot be folded flat for storage and shipping. Examples of patents that disclose molded, filtering, face-piece respirators include U.S. Pat. No. 7,131,442 to Kronzer et al, U.S. Pat. Nos. 6,923,182, 6,041,782 to Angadjivand et al., U.S. Pat. No. 4,873,972 to Magidson et al., U.S. Pat. No. 4,850,347 to Skov, U.S. Pat. No. 4,807,619 to Dyrud et al., U.S. Pat. No. 4,536,440 to Berg, and Des. 285,374 to Huber et al.

Flat-fold respirators—as their name implies—can be folded flat for shipping and storage. They also can be opened into a cup-shaped configuration for use. Examples of flat-fold respirators are shown in U.S. Pat. Nos. 6,568,392 and 6,484,722 to Bostock et al., and U.S. Pat. No. 6,394,090 to Chen.

Although flat-fold respirators are convenient in that they can be folded flat for shipping and storage, these respirators tend to have more difficulty in maintaining their cup-shaped configuration during use. Accordingly, investigators who design flat-fold respirators have provided these masks with weld lines, seams, and folds, to help maintain their cup-shaped configuration during use. Stiffening members also have been incorporated into panels of the mask body (see the Bostock et al. patents cited above).

The present invention, as described below, provides yet another method of improving the structural integrity of a flat-fold filtering face mask during use, and also provides respirator donning and doffing improvements and fit and adjustment benefits to the user.

SUMMARY OF THE INVENTION

The present invention provides a new flat-fold, filtering, face-piece respirator that comprises a harness, a mask body, and first and second flanges. The mask body is capable of being folded flat for storage and can be opened into a cup-shaped configuration for use. The mask body comprises a filtering structure and has the first and second flanges disposed on first and second mask body sides. The first and second flanges project both laterally and frontally from the mask body when opened.

The inventors discovered that the use of first and second flanges on opposing sides of the mask body is beneficial for both maintaining and achieving a snug fit to the wearer's face. The flanges provide a solid surface to which the wearer's fingers can easily grasp the mask to properly position it during donning and subsequent adjustments and doffing. The flanges also act as a lever arm in response to a force from the tension generated by the harness strap. The flanges cause the mask body to be pulled downwardly over the wearer's nose and beneath the eyes and in the region beneath the wearer's chin. The flanges are also beneficial in that they assist in keeping the mask projected outwardly into a cup-shaped configuration away from the wearer's face.

Glossary

The terms set forth below will have the meanings as defined:

"bisect(s)" means to divide into two generally equal parts;

"comprises (or comprising)" means its definition as is standard in patent terminology, being an open-ended term that is generally synonymous with "includes", "having", or "containing". Although "comprises", "includes", "having", and "containing" and variations thereof are commonly-used, open-ended terms, this invention also may be suitably described using narrower terms such as "consists essentially of", which is semi open-ended term in that it excludes only those things or elements that would have a deleterious effect on the performance of the inventive respirator in serving its intended function;

"clean air" means a volume of atmospheric ambient air that has been filtered to remove contaminants;

"contaminants" means particles (including dusts, mists, and fumes) and/or other substances that generally may not be considered to be particles (e.g., organic vapors, et cetera) but which may be suspended in air;

"crosswise dimension" is the dimension that extends laterally across the respirator from side-to-side when the respirator is viewed from the front;

"cup-shaped configuration" means any vessel-type shape that is capable of adequately covering the nose and mouth of a person;

"exterior gas space" means the ambient atmospheric gas space into which exhaled gas enters after passing through and beyond the mask body and/or exhalation valve;

"filtering face-piece" means that the mask body itself is designed to filter air that passes through it; there are no separately identifiable filter cartridges or insert-molded filter elements attached to or molded into the mask body to achieve this purpose;

"filter" or "filtration layer" means one or more layers of air-permeable material, which layer(s) is adapted for the primary purpose of removing contaminants (such as particles) from an air stream that passes through it;

"filter media" means an air-permeable structure that is designed to remove contaminants from air that passes through it;

"filtering structure" means a construction that includes a filter media or a filtration layer;

"first side" means an area of the mask body that is located on one side of a plane that bisects the mask body normal to the cross-wise dimension;

"flange" means a protruding part that imparts structural integrity or strength to the body from which it protrudes;

"frontally" means extending away from the mask body perimeter when the mask body is in a folded condition;

"harness" means a structure or combination of parts that assists in supporting the mask body on a wearer's face;

"integral" means being manufactured together at the same time; that is, being made together as one part and not two separately manufactured parts that are subsequently joined together;

"interior gas space" means the space between a mask body and a person's face;

"laterally" means extending away from a plane that bisects the mask body normal to the cross-wise dimension when the mask body is in a folded condition;

"line of demarcation" means a fold, seam, weld line, bond line, stitch line, hinge line, and/or any combination thereof;

"mask body" means an air-permeable structure that is designed to fit over the nose and mouth of a person and that helps define an interior gas space separated from an exterior gas space (including the seams and bonds that join layers and parts thereof together);

"nose clip" means a mechanical device (other than a nose foam), which device is adapted for use on a mask body to improve the seal at least around a wearer's nose;

"perimeter" means the outer edge of the mask body, which outer edge would be disposed generally proximate to a wearer's face when the respirator is being donned by a person;

"pleat" means a portion that is designed to be or is folded back upon itself;

"polymeric" and "plastic" each mean a material that mainly includes one or more polymers and that may contain other ingredients as well;

"plurality" means two or more;

"respirator" means an air filtration device that is worn by a person to provide the wearer with clean air to breathe;

"second side" means an area of the mask body that is located on one side of a plane that bisects the mask body normal to the cross-wise dimension (the second side being opposite the first side);

"snug fit" or "fit snugly" means that an essentially air-tight (or substantially leak-free) fit is provided (between the mask body and the wearer's face);

"tab" means a part that exhibits sufficient surface area for attachment of another component; and "transversely extending" means extending generally in the crosswise dimension.

DETAILED DESCRIPTION OF PREFERRED EMBODIMENTS

In practicing the present invention, a flat-fold, filtering face-piece respirator is provided that has first and second flanges disposed on first and second opposing sides of the mask body. The first and second flanges have been discovered to be beneficial in providing a more secure fit to the wearer's face. The flanges achieve this face-fitting benefit in a number of ways. Firstly, the flanges assist in providing structural integrity to the mask to keep it in a spaced, cup-shaped configuration, away from the wearer's mouth during use. Flat-fold respirators are not molded into a permanent shape and therefore may have a tendency to lose their desired face-fitting configuration after being worn for extended time periods. The wearer, for example, may inadvertently cause the mask body to bump into external objects during use, and the moisture in exhaled air and the surrounding environment may contribute to loss of shape, causing the mask body interior to contact the wearer's face. The provision of first and second flanges that extend both laterally and frontally from the mask body when in an open configuration assist in maintaining that desired off-the-mouth configuration. Secondly, the first and second flanges provide handles on each side of the mask body to allow the wearer to appropriately adjust the positioning of the mask body during use. The wearer does not need to pinch the outer layers of the mask body to move the mask into a desired face-fitting position. The flanges thus provide a very handy means for accomplishing mask adjustment. Thirdly, the flanges act as structural members that can cause the mask body to be pulled in a downward attitude to better engage the wearer's nose and the area beneath the chin. This particular benefit is described below in more detail with reference to FIG. 6. Fourthly, the flanges provide a means to easily doff the mask, even with gloved hands. Fifthly, once doffed, the flanges can be pulled in opposing directions to quickly re-fold the mask into a flat configuration without further manual manipulation.

Figure 1:
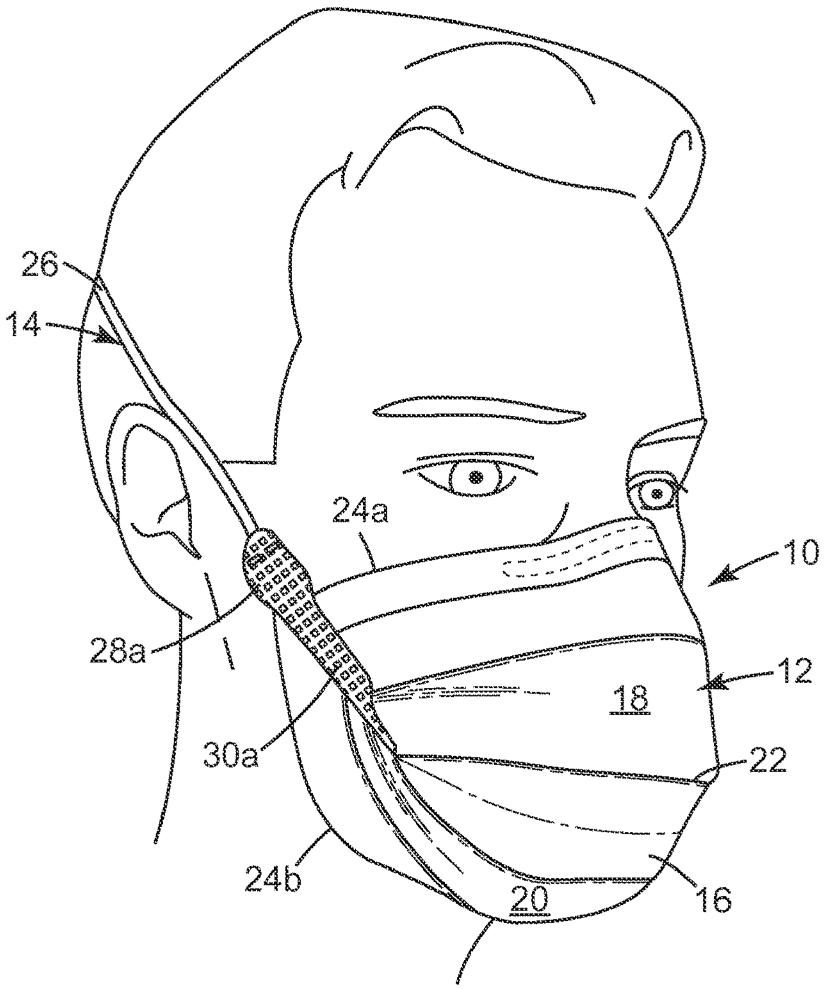
FIG. 1 is a front perspective view of a flat-fold filtering face-piece respirator 10, in accordance with the present invention, being worn on a person's face.

FIG. 1 shows an example of a flat-fold filtering face-piece respirator 10 that may be used in accordance with the present invention to provide clean air for the wearer to breathe. As illustrated, the filtering face-piece respirator 10 includes a mask body 12 and a harness 14. The mask body 12 has a filtering structure 16 through which inhaled air must pass before entering the wearer's respiratory system. The filtering structure 16 removes contaminants from the ambient environment so that the wearer breathes clean air. The mask body 12 includes a top portion 18 and a bottom portion 20. The top portion 18 and the bottom portion 20 are separated by a line of demarcation 22. In this particular embodiment, the line of demarcation 22 is a pleat that extends transversely across the central portion of the mask body. The mask body 12 also includes a perimeter that includes an upper segment 24*a* and a lower segment 24*b*. The harness 14 has a strap 26 that is stapled to a tab 28*a*. As illustrated, the tab 28*a* is an integral part of the flange 30*a*.

Figure 2:
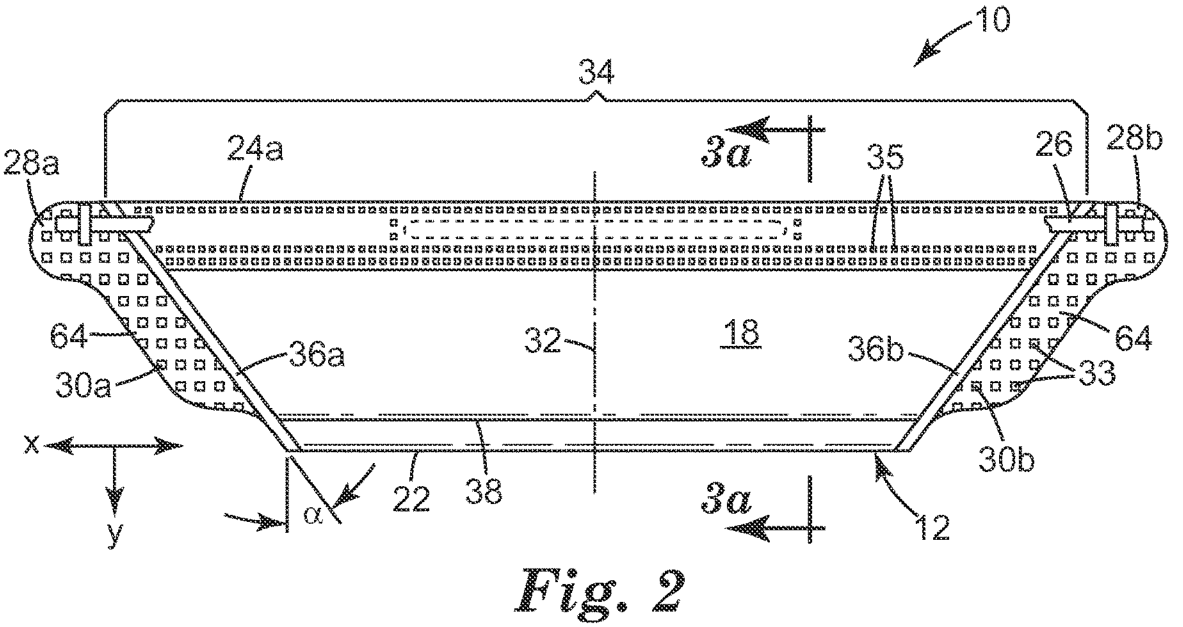
FIG. 2 is a top view of the respirator 10 shown in FIG. 1.

FIG. 2 illustrates that the respirator 10 can have first and second flanges 30*a* and 30*b* located on opposing sides of the mask body 12. The strap 26 is stapled to each tab 28*a*, 28*b*.

The flanges 30a and 30b project both laterally and frontally from the mask body. The flange projects laterally from the mask body in that it extends away from a plane 32 that bisects the mask body in the x directions. The flanges 30a and 30b also extend frontally from the mask body 12 in that they extend away from the perimeter 24a towards the front edge 22 of the mask body 12 as noted by arrow y. Each flange typically occupies a surface area of about 1 to 15 square centimeters, more typically about 2 to 12 square centimeters, still more typically about 5 to 10 square centimeters. The flanges also typically extend away from the mask body at least 2 millimeters (mm), more typically at least 5 mm, and still more typically at least 1 to 2 centimeters (cm). The flanges 30a, 30b may be integrally or non-integrally disposed on the mask body and may comprise one or more or all of the various layers that comprise the mask body. That is, the flanges may be an extension of the material used to make the mask body or they may be made from a separate material such as a rigid or semi-rigid plastic. An integral flange can have welds or bonds 33 provided thereon to increase flange stiffness. Alternatively, an adhesive layer may be used to increase flange stiffness. Using the Stiffness in Flexure Test set forth below, the flanges may have a flexural modulus of at least 10 Mega Pascals (MPa), more typically at least 20 MPa when bent along a major surface of the flange. At the upper end, the flexural modulus is typically less than 100 MPa, more typically less than 60 MPa. These numbers (i.e., at both the low and high ends) are approximately twice as large when the test is performed along the edges of the sample. Although the tabs 28a and 28b are illustrated in FIG. 2 as having a shared edge that is part of perimeter segment 24a, the tabs, however may extend beyond the face-contacting periphery part of the mask body perimeter when the mask is placed upon a wearer's face as shown in FIG. 1. The face-contacting periphery generally resides within the bracketed area 34 and thus is not part of the tab perimeter. The mask body perimeter may have a series of bonds or welds 35 to join the various layer layers of the mask body 12 together. The mask body 12 also includes first and second lines of demarcation 36a, 36b located on first and second sides of the mask body 12. The first and second flanges 30a, 30b are joined to the mask body at the first and second lines of demarcation 36a, 36b and may be rotated about an axis parallel these demarcation lines, respectively. The first and second lines of demarcation 36a, 36b are off-set at an angle α from plane 32 that extends perpendicular to the perimeter 24a of the mask body 12 when viewing the mask body from the top view in a folded condition. The angle α may be from zero to about 60 degrees, more typically about 30 to 45 degrees. The upper portion 18 includes at least one pleat line 38 that extends from the first line of demarcation 36a to the second line of demarcation 36b transversely.

Figure 3A:
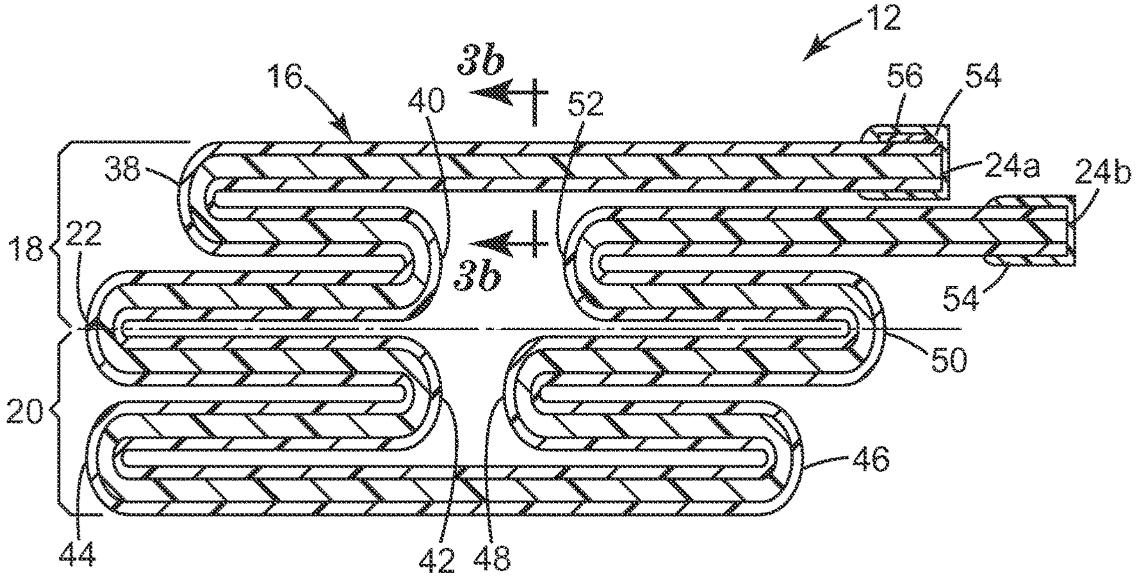
FIG. 3*a* is a cross-sectional view of the mask body 12 taken along lines 3*a*-3*a* of FIG. 2.

FIG. 3a illustrates an example of a pleated configuration of a mask body 12 in accordance with the present invention. As shown, the mask body 12 includes pleats 22 and 38, already described with reference to FIGS. 1 and 2. The upper portion or panel 18 of the mask body 12 also includes pleat 40. The lower portion or panel 20 of the mask body 12 includes pleats 42, 44, 46, 48, 50, and 52. The lower portion 20 of the mask body 12 may include more filter media surface area than the upper portion 18. The mask body 12 also includes a perimeter web 54 that is secured to the mask body along its perimeter. The perimeter web 54 may be folded over the mask body at the perimeter 24a, 24b. The perimeter web 54 may also be an extension of the inner cover web 58 folded and secured around the edge of 24a and 24b. A nose clip 56 may be disposed on the upper portion 18 of the mask body centrally adjacent to the perimeter between the filtering structure 16 and the perimeter web 54. The nose clip 56 may be made from a pliable metal or plastic that is capable of being manually adapted by the wearer to fit the contour of the wearer's nose. As shown, the upper portion 18 appears as a pleated panel when the mask body 12 is in a folded condition; similarly the lower portion 20 (FIG. 1) appears as a pleated panel when the mask is in its folded storage condition.

Figure 3B:
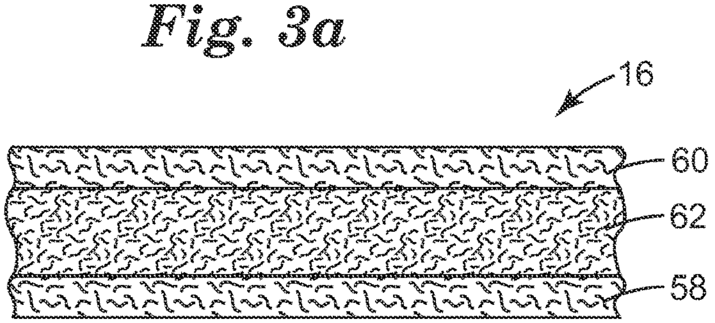
FIG. 3*b* is a cross-sectional view of the filtering structure 16 taken along lines 3*b*-3*b* of FIG. 3*a*.

FIG. 3b illustrates that the filtering structure 16 may include one or more layers such as an inner cover web 58, an outer cover web 60, and a filtration layer 62. The inner and outer cover webs 58 and 60 may be provided to protect the filtration layer 62 and to preclude fibers from the filtration layer 62 from coming loose and entering the mask interior. During respirator use, air passes sequentially through layers 60, 62, and 58 before entering the mask interior. The air that is disposed within the interior gas space of the mask may then be inhaled by the wearer. When a wearer exhales, the air passes in the opposite direction sequentially through layers 58, 62, and 60. Alternatively, an exhalation valve (not shown) may be provided on the mask body to allow exhaled air to be rapidly purged from the interior gas space to enter the exterior gas space without passing through filtering structure 16. Typically, the cover webs 58 and 60 are made from a selection of nonwoven materials that provide a comfortable feel, particularly on the side of the filtering structure that makes contact with the wearer's face. The construction of various filter layers and cover webs that may be used in conjunction with the support structure of the present invention are described below in more detail. To improve wearer fit and comfort, an elastomeric face seal can be secured to the perimeter of the filtering structure 16. Such a face seal may extend radially inward to contact the wearer's face when the respirator is being donned. Examples of face seals are described in U.S. Pat. No. 6,568,392 to Bostock et al., U.S. Pat. No. 5,617,849 to Springett et al., and U.S. Pat. No. 4,600,002 to Maryyanek et al., and in Canadian Patent 1,296,487 to Yard. The filtering structure also may have a structural netting or mesh juxtaposed against at least one or more of the layers 58, 60, or 62, typically against the outer surface of the outer cover web 60. The use of such a mesh is described in U.S. patent application Ser. No. 12/338,091, filed on the same day as this patent application, entitled Expandable Face Mask with Reinforcing Netting (attorney case no. 65000US002).

Figure 4:
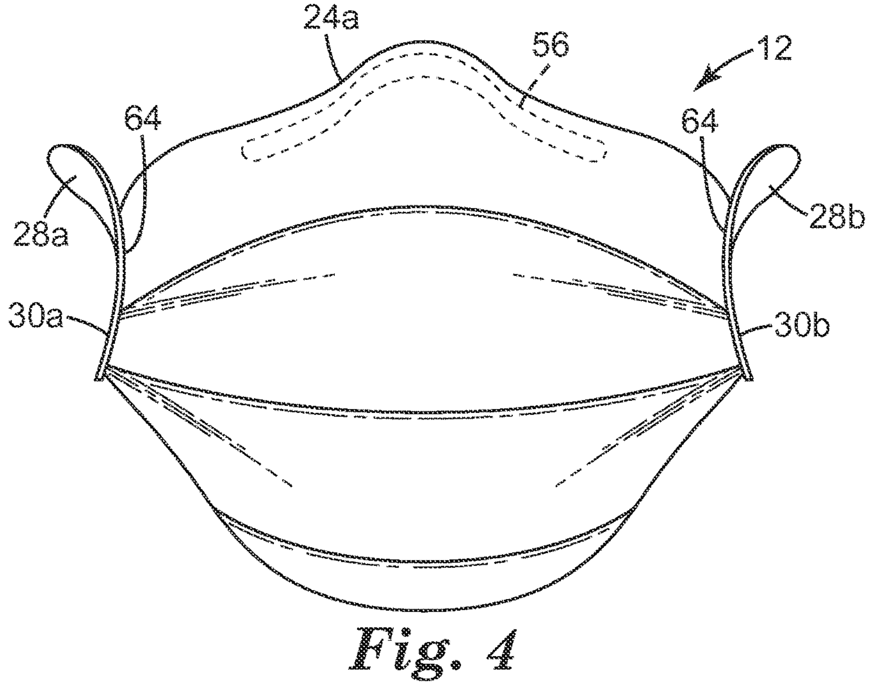
FIG. 4 is a front view of the mask body 12, which may be used in connection with the present invention.

FIG. 4 shows the mask body 12 in an in-use configuration. During use, the flanges 30a, 30b may be disposed on the first and second sides of the mask body such that they become folded inward towards the mask body during use. If desired, the mask body and/or the contacting side of the flanges 30a, 30b may have a securing means that enables each flange 30a, 30b to be joined to the mask body on a major surface 64 of the flange. Such a securing means may include an adhesive and release liner, a hook-and-loop type fastener, or any other suitable chemical, physical, or mechanical type fastener.

Figure 5:
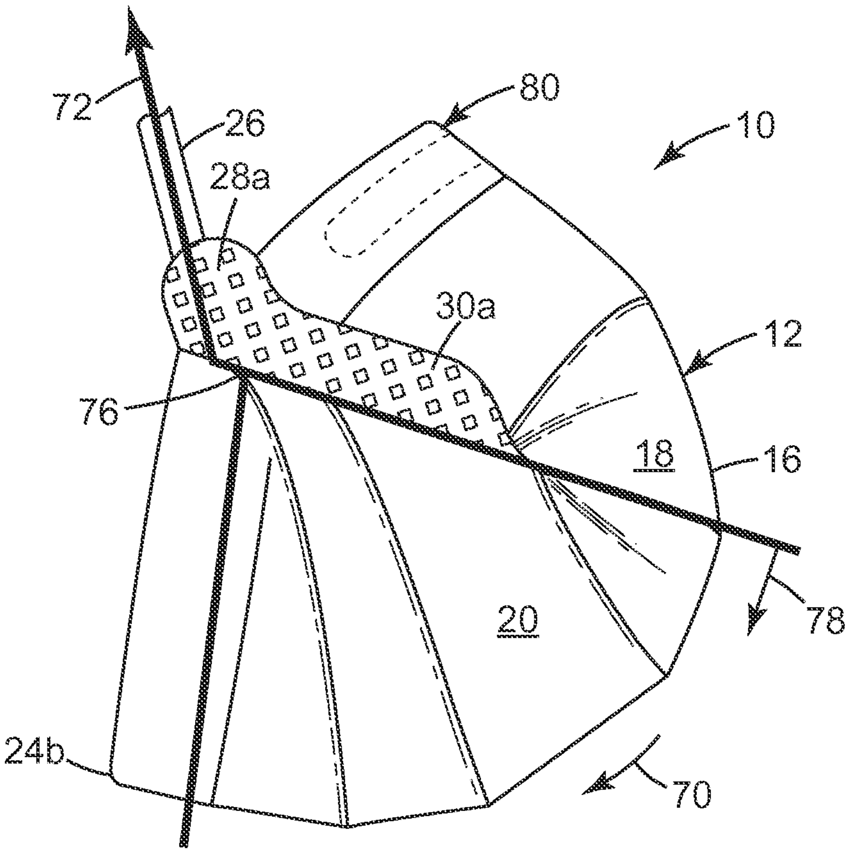
FIG. 5 is a side view of the respirator 10, illustrating how the flanges may contribute to improved fit.

FIG. 5 schematically illustrates how the tension from the harness strap 26 can exert a force that is directed along the length of the flange 30a so as to cause the mask body to be pulled in a downward direction as noted by the arrow 70. When a wearer dons respirator 10, the strap 26 is disposed behind the wearer's head above the ears. Because the strap is fastened to engage the head above the ears, the strap pulls upwardly on the mask body as noted in the direction of arrow 72. The force that travels in the direction of arrow 72 pulls upon the tab 28*a* in a similar direction. The mask body has a fulcrum in the general area of intersection point 76, which enables a force to be transferred along the mask body where the flange 30*a* is secured thereto. Because of the fulcrum 76, the flange 30*a* tends to drive the mask body downwardly in the direction of arrow 78. The complementary force that is exerted by the flange 30*a* in the direction of arrow 78 causes the mask to more snugly engage the wearer's nose in nose region 80. The force transfer also tends to make the mask body more tightly engaged with the wearer's face beneath the chin along perimeter 24*b*. The use of first and second flanges 30*a* and 30*b* thus may allow an improved snug fit to be achieved in a flat-fold filtering face mask. Further, the provision of first and second flanges 30*a* and 30*b* allows the wearer to more easily grasp the mask at those locations so that the mask body can be more easily manipulated into its appropriate position on the wearer's face. The use of flanges 30*a* and 30*b* also enables only one strap to be used on a mask body to achieve a very good snug fit to a wearer's face.

The filtering structure that is used in connection with the present invention may take on a variety of different shapes and configurations. The filtering structure typically is adapted so that it properly fits against or within the support structure. Generally the shape and configuration of the filtering structure corresponds to the general shape of the mask body. Although a filtering structure has been illustrated with multiple layers that include a filtration layer and two cover webs, the filtering structure may simply comprise a filtration layer or a combination of filtration layers. For example, a pre-filter may be disposed upstream to a more refined and selective downstream filtration layer. Additionally, sorptive materials such as activated carbon may be disposed between the fibers and/or various layers that comprise the filtering structure. Further, separate particulate filtration layers may be used in conjunction with sorptive layers to provide filtration for both particulates and vapors. The filtering structure may include one or more stiffening layers that assist in providing a cup-shaped configuration. The filtering structure also could have one or more horizontal and/or vertical lines of demarcation that contribute to its structural integrity. Using the first and second flanges in accordance with the present invention, however, may make unnecessary the need for such stiffening layers and lines of demarcation.

The filtering structure that is used in a mask body of the invention can be of a particle capture or gas and vapor type filter. The filtering structure also may be a barrier layer that prevents the transfer of liquid from one side of the filter layer to another to prevent, for instance, liquid aerosols or liquid splashes (e.g. blood) from penetrating the filter layer. Multiple layers of similar or dissimilar filter media may be used to construct the filtering structure of the invention as the application requires. Filters that may be beneficially employed in a layered mask body of the invention are generally low in pressure drop (for example, less than about 195 to 295 Pascals at a face velocity of 13.8 centimeters per second) to minimize the breathing work of the mask wearer. Filtration layers additionally are flexible and have sufficient shear strength so that they generally retain their structure under the expected use conditions. Examples of particle capture filters include one or more webs of fine inorganic fibers (such as fiberglass) or polymeric synthetic fibers. Synthetic fiber webs may include electret-charged polymeric microfibers that are produced from processes such as melt-blowing. Polyolefin microfibers formed from polypropylene that has been electrically charged provide particular utility for particulate capture applications. An alternate filter layer may comprise a sorbent component for removing hazardous or odorous gases from the breathing air. Sorbents may include powders or granules that are bound in a filter layer by adhesives, binders, or fibrous structures—see U.S. Pat. No. 6,334,671 to Springett et al. and U.S. Pat. No. 3,971,373 to Braun. A sorbent layer can be formed by coating a substrate, such as fibrous or reticulated foam, to form a thin coherent layer. Sorbent materials may include activated carbons that are chemically treated or not, porous alumna-silica catalyst substrates, and alumna particles. An example of a sorptive filtration structure that may be conformed into various configurations is described in U.S. Pat. No. 6,391,429 to Senkus et al.

The filtration layer is typically chosen to achieve a desired filtering effect. The filtration layer generally will remove a high percentage of particles and/or or other contaminants from the gaseous stream that passes through it. For fibrous filter layers, the fibers selected depend upon the kind of substance to be filtered and, typically, are chosen so that they do not become bonded together during the molding operation. As indicated, the filtration layer may come in a variety of shapes and forms and typically has a thickness of about 0.2 millimeters (mm) to 1 centimeter (cm), more typically about 0.3 mm to 0.5 cm, and it could be a generally planar web or it could be corrugated to provide an expanded surface area—see, for example, U.S. Pat. Nos. 5,804,295 and 5,656,368 to Braun et al. The filtration layer also may include multiple filtration layers joined together by an adhesive or any other means. Essentially any suitable material that is known (or later developed) for forming a filtering layer may be used as the filtering material. Webs of melt-blown fibers, such as those taught in Wente, Van A., Superfine Thermoplastic Fibers, 48 Indus. Engn. Chem., 1342 et seq. (1956), especially when in a persistent electrically charged (electret) form are especially useful (see, for example, U.S. Pat. No. 4,215,682 to Kubik et al.). These melt-blown fibers may be microfibers that have an effective fiber diameter less than about 20 micrometers (μm) (referred to as BMF for "blown microfiber"), typically about 1 to 12 μm. Effective fiber diameter may be determined according to Davies, C. N., *The Separation Of Airborne Dust Particles*, Institution Of Mechanical Engineers, London, Proceedings 1B, 1952. Particularly preferred are BMF webs that contain fibers formed from polypropylene, poly(4-methyl-1-pentene), and combinations thereof. Electrically charged fibrillated-film fibers as taught in van Turnhout, U.S. Pat. No. Re. 31,285, also may be suitable, as well as rosin-wool fibrous webs and webs of glass fibers or solution-blown, or electrostatically sprayed fibers, especially in microfilm form. Electric charge can be imparted to the fibers by contacting the fibers with water as disclosed in U.S. Pat. No. 6,824,718 to Eitzman et al., U.S. Pat. No. 6,783,574 to Angadjivand et al., U.S. Pat. No. 6,743,464 to Insley et al., U.S. Pat. Nos. 6,454,986 and 6,406,657 to Eitzman et al., and 6,375,886 and 5,496,507 to Angadjivand et al. Electric charge also may be imparted to the fibers by corona charging as disclosed in U.S. Pat. No. 4,588,537 to Klasse et al. or by tribocharging as disclosed in U.S. Pat. No. 4,798,850 to Brown. Also, additives can be included in the fibers to enhance the filtration performance of webs produced through the hydro-charging process (see U.S. Pat. No. 5,908,598 to Rousseau et al.). Fluorine atoms, in particular, can be disposed at the surface of the fibers in the filter layer to improve filtration performance in an oily mist environment—see U.S. Pat. Nos. 6,398,847 B1, 6,397,458 B1, and 6,409,806 B1 to Jones et al. Typical basis weights for electret BMF filtration layers are about 10 to 100 grams per square meter. When electrically charged according to techniques described in, for example, the '507 Angadjivand et al. patent, and when including fluorine atoms as mentioned in the Jones et al. patents, the basis weight may be about 20 to 40 g/m and about 10 to 30 g/m, respectively.

An inner cover web can be used to provide a smooth surface for contacting the wearer's face, and an outer cover web can be used to entrap loose fibers in the mask body or for aesthetic reasons. The cover web typically does not provide any substantial filtering benefits to the filtering structure, although it can act as a pre-filter when disposed on the exterior (or upstream to) the filtration layer. To obtain a suitable degree of comfort, an inner cover web preferably has a comparatively low basis weight and is formed from comparatively fine fibers. More particularly, the cover web may be fashioned to have a basis weight of about 5 to 50 $g/m^2$ (typically 10 to 30 $g/m^2$), and the fibers may be less than 3.5 denier (typically less than 2 denier, and more typically less than 1 denier but greater than 0.1). Fibers used in the cover web often have an average fiber diameter of about 5 to 24 micrometers, typically of about 7 to 18 micrometers, and more typically of about 8 to 12 micrometers. The cover web material may have a degree of elasticity (typically, but not necessarily, 100 to 200% at break) and may be plastically deformable.

Suitable materials for the cover web may be blown microfiber (BMF) materials, particularly polyolefin BMF materials, for example polypropylene BMF materials (including polypropylene blends and also blends of polypropylene and polyethylene). A suitable process for producing BMF materials for a cover web is described in U.S. Pat. No. 4,013,816 to Sabee et al. The web may be formed by collecting the fibers on a smooth surface, typically a smooth-surfaced drum or a rotating collector—see U.S. Pat. No. 6,492,286 to Berrigan et al. Spun-bond fibers also may be used.

A typical cover web may be made from polypropylene or a polypropylene/polyolefin blend that contains 50 weight percent or more polypropylene. These materials have been found to offer high degrees of softness and comfort to the wearer and also, when the filter material is a polypropylene BMF material, to remain secured to the filter material without requiring an adhesive between the layers. Polyolefin materials that are suitable for use in a cover web may include, for example, a single polypropylene, blends of two polypropylenes, and blends of polypropylene and polyethylene, blends of polypropylene and poly(4-methyl-1-pentene), and/or blends of polypropylene and polybutylene. One example of a fiber for the cover web is a polypropylene BMF made from the polypropylene resin "Escorene 3505G" from Exxon Corporation, providing a basis weight of about 25 $g/m^2$ and having a fiber denier in the range 0.2 to 3.1 (with an average, measured over 100 fibers of about 0.8). Another suitable fiber is a polypropylene/polyethylene BMF (produced from a mixture comprising 85 percent of the resin "Escorene 3505G" and 15 percent of the ethylene/alpha-olefin copolymer "Exact 4023" also from Exxon Corporation) providing a basis weight of about 25 $g/m^2$ and having an average fiber denier of about 0.8. Suitable spunbond materials are available, under the trade designations "Corosoft Plus 20", "Corosoft Classic 20" and "Corovin PP-S-14", from Corovin GmbH of Peine, Germany, and a carded polypropylene/viscose material available, under the trade designation "370/15", from J. W. Suominen OY of Nakila, Finland.

Cover webs that are used in the invention preferably have very few fibers protruding from the web surface after processing and therefore have a smooth outer surface. Examples of cover webs that may be used in the present invention are disclosed, for example, in U.S. Pat. No. 6,041,782 to Angadjivand, U.S. Pat. No. 6,123,077 to Bostock et al., and WO 96/28216A to Bostock et al.

The strap(s) that are used in the harness may be made from a variety of materials, such as thermoset rubbers, thermoplastic elastomers, braided or knitted yarn/rubber combinations, inelastic braided components, and the like. The strap(s) may be made from an elastic material such as an elastic braided material. The strap preferably can be expanded to greater than twice its total length and be returned to its relaxed state. The strap also could possibly be increased to three or four times its relaxed state length and can be returned to its original condition without any damage thereto when the tensile forces are removed. The elastic limit thus is preferably not less than two, three, or four times the length of the strap when in its relaxed state. Typically, the strap(s) are about 20 to 30 cm long, 3 to 10 mm wide, and about 0.9 to 1.5 mm thick. The strap(s) may extend from the first tab to the second tab as a continuous strap or the strap may have a plurality of parts, which can be joined together by further fasteners or buckles. For example, the strap may have first and second parts that are joined together by a fastener that can be quickly uncoupled by the wearer when removing the mask body from the face. An example of a strap that may be used in connection with the present invention is shown in U.S. Pat. No. 6,332,465 to Xue et al. Examples of fastening or clasping mechanism that may be used to joint one or more parts of the strap together is shown, for example, in the following U.S. Pat. No. 6,062,221 to Brostrom et al., U.S. Pat. No. 5,237,986 to Seppala, and EP1,495,785A1 to Chien.

As indicated, an exhalation valve may be attached to the mask body to facilitate purging exhaled air from the interior gas space. The use of an exhalation valve may improve wearer comfort by rapidly removing the warm moist exhaled air from the mask interior. See, for example, U.S. Pat. Nos. 7,188,622, 7,028,689, and 7,013,895 to Martin et al.; U.S. Pat. No. 7,428,903, 7,311,104, 7,117,868, 6,854,463, 6,843,248, and 5,325,892 to Japuntich et al.; U.S. Pat. No. 6,883,518 to Mittelstadt et al.; and RE37,974 to Bowers. Essentially any exhalation valve that provides a suitable pressure drop and that can be properly secured to the mask body may be used in connection with the present invention to rapidly deliver exhaled air from the interior gas space to the exterior gas space.

A nose clip that is used in conjunction with the present invention may be essentially any additional part that assists in improving the fit over the wearer's nose. Because there are substantial changes in contour to the wearer's face in this region, a nose clip can better assist the mask body in achieving the appropriate fit in this location. The nose clip may comprise, for example, a pliable dead soft band of metal such as aluminum, which can be shaped to hold the mask in a desired fitting relationship over the nose of the wearer and where the nose meets the cheek. An example of a suitable nose clip is shown in U.S. Pat. No. 5,558,089 and Des. 412,573 to Castiglione. Other nose clips are described in U.S. patent application Ser. No. 12/238,737 (filed Sep. 26, 2008); U.S. Publications 2007-0044803A1 (filed Aug. 25, 2005); and 2007-0068529A1 (filed Sep. 27, 2005).

EXAMPLES

Stiffness in Flexure Test

Flange stiffness was measured via a modified ASTM D790 method "Flexural Properties of Unreinforced and Reinforced Plastics and Electrical Insulating Materials," Method I "Three Point Bend Testing". Flexural Modulus was calculated according to ASTM D790 in the linear region of the stress-strain plot. Values of Flexural Modulus were recorded in units of megapascal (MPa).

Dimensions of tested samples were 19 mm×23 mm×2 mm. Span was set at 15 millimeters (mm) with a nose radius was 2.5 mm. Crosshead speed was set at 13 mm/min. A 100 load frame from MTS Alliance, Eden Prairie, Minn. was used for all testing.

Respirator Assembly

Example 1

A respirator filtering structure was formed from three layers of nonwoven material and other respirator components. The inventive mask was assembled in two operations—preform making and mask finishing. The preform making stage included the steps of lamination and fixing of nonwoven fibrous webs, formation of pleat crease lines and attachment of perimeter web material and nose clip. The mask finishing operation included folding of pleats along embossed crease lines, fusing both the lateral mask edges and reinforced flange material, cutting the final form, and attaching a headband.

In the preform making stage three layers of nonwoven material were plied in face to face orientation. In the example, individual materials that formed the layers were assembled in the following order:

1. outer Netting/Scrim
2. filter material
3. inner cover web

The outer netting/scrim was a lamination of a Thermanet 5103 netting, (available from Conwed, Minneapolis, Minn.) that was bonded to a 17 grams/meter square (gms) Elite 050 scrim, from Leggett and Platt-Hanes Industries, Carthage, Mo. The netting/scrim laminate, indicated as 60 in FIG. 3*b*, was formed in a thermal bonding step that used heat and compression to melt-bond the strands of the netting onto the scrim. The netting/scrim layer had a total thickness of 0.12 mm with the scrim thickness 0.10 mm. Filter material (indicated as 62 in FIG. 3*b*) used in the preform was an electret-charged blown microfiber polypropylene web with a basis weight of 35 gms, a solidity of 8% and an effective fiber size of 4.75 micrometers. The inner cover web (indicated as 58 in FIG. 3*b*) was a 17 gms spun-bonded polypropylene scrim, available from BBA Nonwovens, Charlotte, N.C. The preform was made by plying, in the desired order, layers of each material that was then cut into 20 cm by 33 cm sheets and ultrasonically welded together using a point-bonded pattern. Ultrasonic welding was done using an ultrasonic welding unit, model 2000, from Branson, Danbury, Conn., operated at a ram pressure of 483 kilo pascals (kPa) with a horn amplitude, frequency, and dwell time of 100%, 20 kHz and 0.7 sec respectively. Operating against an anvil with flat-top square pegs, having individual face areas of 1.6 square millimeters arranged in a grid pattern with spacing of approximately one centimeter on center of the pegs the flat-faced horn of the welder acted against the anvil with a contact pressure of approximately 6 MPa. With the layers of nonwoven fixed, crease lines that define pleat location were embossed on the fixed layers of nonwoven. Embossing of the crease lines was done using a die cutting machine, Hytronic Cutting Machine Model B, from USM Corporation, Haverhill, Mass., at 15 tons of force and with a rule die. The die had nine bars with radius edges that traversed the length of the preform and when pressed into the preform created lines into the nonwoven layers. The embossed lines compressed the webs together at the point of contact and did not fuse or penetrate the material. As a final step in the preform making operation, bands of perimeter web, BBA Nonwovens, 51 grams per square meter (gsm) spun-bonded polypropylene scrim, 4 cm wide and 36 cm long were wrapped around the top and bottom edges of the preform and ultrasonically welded into place. Ultrasonic welding was carried out using an ultrasonic welding unit Model 2000× from Branson, Danbury, Conn., operated at a ram pressure of 448 kPa with a horn amplitude, frequency, and dwell time of 100%, 20 kHz, and 0.5 sec, respectively. Operating against an anvil with a contact surface area of 4.1 square centimeters, using the specified ram pressure and horn conditions, resulted in contact pressures of 8.5 MPa to bond the materials of the preform. The area of the anvil used to bond the perimeter web material was configured in flat-top square pegs, having individual face areas of 1.6 square millimeters that were arranged in a pattern 35 shown in FIG. 2. The flat-faced horn of the welder acted against an anvil, fixing the perimeter web to the preform. Using this process, a nose clip was attached to the top of the preform and was encapsulated between the preform and the perimeter web. The nose clip was a malleable, plastically-deformable aluminum strip that had the shape shown in FIG. 2 and was 9 cm long by 0.5 cm wide by 1 mm thick.

In the mask finishing operation, pleats were folded along crease lines as shown in FIG. 3. Pleats located above the central fold of the mask, were folded such that the exterior folds faced downwards with the mask open, this was done to help prevent accumulation of gross matter in the mask folds when worn. With the preform properly pleated and folded around the center fold, the preform was ultrasonically welded to fuse the lateral edges of the mask (36*a* and 36*b* in FIG. 2) and to create the bonded layers of the stiffening flange (30*a* and 30*b* in FIG. 2). Ultrasonic welding was done using an ultrasonic welding unit Model 2000ae from Branson, Danbury, Conn., operated at a ram pressure of 483 kPa with a horn amplitude, frequency, and dwell time of 100%, 20 kHz, and 2.0 sec, respectively. Operating against an anvil with a contact surface area of 22.4 square centimeters, using the specified ram pressure and horn conditions, resulted in contact pressures of 1.5 MPa to bond the materials of the preform. The contact area of the anvil for bonding the flange material was configured in flat-top square pegs, having individual face areas of 1.6 square millimeters that were spaced 1.27 millimeters apart from their flat sides, the resultant bond pattern is indicated as 30*a* in FIG. 5. The anvil bars that formed the lateral edge bonds of the mask were 95.25 millimeters long and 9.525 millimeters wide, with the resulting bond pattern indicated as 36*a* in FIG. 2. The flat-faced horn of the welder acted against the anvil resulting in the formation of a weld pattern (33 in FIG. 2) and created the bonded layers of the flanges. Angled bar elements of the anvil sealed the lateral edges of the mask and pin welding surfaces fused and stiffened the flange material. As a final step in the mask finishing operation, the stiffening flanges were cut to a desired shape and a headband was stapled to the tabs. Flanges were 1.0 cm wide by 5.0 cm long with a 0.5 cm radius head located at the tab point of attachment of the headband. The headband was attached to the tabs radius head using a hand stapler from Stanley Bostitch, East Greenwich, R.I., model P6C-8 and staples No. STH5019 ¼ inch galvanized. Sections of the flange were cut from the mask and tested according to the method outlined in Stiffness in Flexure Test. The flange sections were tested in two orientations: along the flat plane of the sample and along the edge of the sample as it would be oriented along the length of the flange. When bent along the flat plane of the sample, the flexural modulus was 27 MPa. When tested along the edge of the sample, it was 66 MPa. The headband was 7.9 mm wide by 0.8 mm thick, Sample No. 125-1 from Providence Braid Co., Pawtucket, R.I. The flanges were able to rotate on an axis parallel to the line of attachment to the mask body and provided a more rigid mask body when opened and donned.

Example 2

The respirator was made from of the same materials and in the manner of Example 1 except that a separate plastic sheet was used for the flanges. Using a mask body as formed in Example 1, the nonwoven flanges were removed and replaced with sheets of polyethylene film, 0.7 mm thick from McMaster-Carr, Chicago, Ill., that were cut into the same shape and size of the removed flanges. The plastic flanges were attached to the mask by ultrasonic welding using a hand-held ultrasonic horn from Branson, Danbury, Conn., Model E-150B. The horn of the welder was configured with a rectangular bar on its face, 13 mm long and 2 mm wide, that contacted the material to be bonded and compressed it against a flat anvil. The welder was operated with an applied contact pressure of approximately 3.4 MPa and a horn amplitude, frequency, and dwell time of 100%, 20 kHz, and 1.0 sec, respectively. The film stiffing flange provided good rigidity and stiffness.

Example 3

The respirator was made from the same materials and in the manner of Example 1 except that a securement means was located along one major surface of the flange so that the flange could be pressed into securement with the mask body. The flange was secured to the mask body by removing the release liner and pressing the flange onto the mask body. The securement means held the stiffening flange in a near vertical orientation against the mask body when in an opened configuration. By affixing the flange in this manner, the mask was supported in an open position even without being worn. With the flange fixed to the mask body, the mask body was further rigidified and acted in response to the lever action of the flange in response to a force from the harness strap. The securement means was a section of pressure sensitive Hi-Strength Acrylic adhesive on a Polycoated Kraft paper release liner, Scotch™ Laminating Adhesive 9671, 3M Company, St. Paul Minn. The adhesive was applied to the top major surface of the flange so that it would contact the mask body when rotated towards it along the line of demarcation axis.

This invention may take on various modifications and alterations without departing from its spirit and scope. Accordingly, this invention is not limited to the above-described but is to be controlled by the limitations set forth in the following claims and any equivalents thereof.

This invention also may be suitably practiced in the absence of any element not specifically disclosed herein.

All patents and patent applications cited above, including those in the Background section, are incorporated by reference into this document in total. To the extent there is a conflict or discrepancy between the disclosure in such incorporated document and the above specification, the above specification will control.

What is claimed is:

1. A flat-fold filtering face-piece respirator that comprises:

a harness;

a mask body that has a perimeter including a periphery that is adapted to contact a face of a wearer when the flat-fold filtering face-piece respirator is in use, wherein the mask body is capable of being folded flat into a folded condition for storage and opened into a cup-shaped configuration for use, and that comprises a filtering structure; and first and second flanges that are disposed on first and second sides of the mask body and joined to the mask body at first and second lines of demarcation located on the first and second sides of the mask body, wherein each of the first and second flanges project both laterally and frontally from the mask body when the mask body is in the folded condition, wherein the first and second flanges are adapted to fold inward towards the mask body during use of the flat-fold filtering face-piece respirator by being rotated about an axis parallel to the first and second lines of demarcation.

2. The flat-fold filtering face-piece respirator of claim 1, wherein the harness includes a strap that has first and second ends that are attached to first and second tabs that are integral to the first and second flanges, respectively.

3. The flat-fold filtering face-piece respirator of claim 1, wherein the first and second lines of demarcation are offset at an angle $\alpha$ of 30 to 45 degrees from a line that extends perpendicular to the perimeter of the mask body when viewing the mask body from a top view in the folded condition.

4. The flat-fold filtering face-piece respirator of claim 1, wherein the mask body comprises first and second panels when in the folded condition, and wherein at least one of the panels comprises one or more pleats that extend from the first line of demarcation to the second line of demarcation.

5. The flat-fold filtering face-piece respirator of claim 1, wherein the mask body comprises a plurality of layers, wherein the first and second flanges comprise one or more of the plurality of layers that comprise the mask body, and wherein the flanges are integral to the mask body.

6. The flat-fold filtering face-piece respirator of claim 5, wherein the first and second flanges each have a means for increasing flange stiffness.

7. The flat-fold filtering face-piece respirator of claim 6, wherein the means for increasing flange stiffness includes a weld pattern.

8. The flat-fold filtering face-piece respirator of claim 5, wherein the flanges each occupy a surface area of 2 to 12 square centimeters.

9. The flat-fold filtering face-piece respirator of claim 8, wherein the flanges each occupy a surface area of 5 to 10 square centimeters.

10. The flat-fold filtering face-piece respirator of claim 8, wherein the flanges each extend away from the mask body at least 2 millimeters.

11. The flat-fold filtering face-piece respirator of claim 10, wherein the first and second flanges each extend away from the mask body at least 5 millimeters.

12. The flat-fold filtering face-piece respirator of claim 11, wherein the first and second flanges each extend away from the mask body at least 1 centimeter.

13. The flat-fold filtering face-piece respirator of claim 5, further comprising a fastener adapted to secure a major surface of each of the first and second flanges to the mask body when the first and second flanges are folded inward towards the mask body during use of the flat-fold filtering face-piece respirator.

14. The flat-fold filtering face-piece respirator of claim 13, wherein the fastener comprises an adhesive.

15. The flat-fold filtering face-piece respirator of claim 14, further comprising a release liner that covers the adhesive until use.

16. The flat-fold filtering face-piece respirator of claim 1, wherein the mask body is capable of taking on the folded condition by grasping the first and second flanges and pulling manually thereon in opposing directions away from a plane that bisects the mask body without further manual manipulation.

17. The flat-fold filtering face-piece respirator of claim 1, wherein the flanges each have a flexural modulus of at least 10 MPa when bent along a major surface of the flange using the Stiffness in Flexure Test.

18. The flat-fold filtering face-piece respirator of claim 17, wherein the flanges each have a flexural modulus of at least 20 MPa.

19. The flat-fold filtering face-piece respirator of claim 1, wherein the first and second flanges do not form part of the periphery.

20. The flat-fold filtering face-piece respirator of claim 1, wherein the filtering structure contains a plurality of layers, at least one of which is a filtration layer, and wherein the first and second flanges comprise all of the plurality of layers in the filtering structure of the mask body.

21. The flat-fold filtering face-piece respirator of claim 20, wherein the first and second flanges are integral to the mask body and are an extension of the plurality of layers in the mask body.

22. A flat-fold filtering face-piece respirator that comprises:

a harness;

a mask body that has a periphery that is adapted to contact a face of a wearer when the flat-fold filtering face-piece respirator is in use, wherein the mask body is capable of being folded flat into a folded condition for storage and opened into a cup-shaped configuration for use, and that comprises a filtering structure that contains a plurality of layers, including a cover web and a filtration layer; and first and second flanges that are not part of the periphery and that are disposed on first and second sides of the mask body integral thereto at first and second lines of demarcation located on the first and second sides of the mask body, each of the first and second flanges projecting both laterally and frontally from the mask body when the mask body is in the folded condition, wherein each of the first and second flanges comprises all of the plurality of layers that comprise the filtering structure and have the plurality of layers welded together, and further wherein the first and second flanges are adapted to fold inward towards the mask body during use of the flat-fold filtering face-piece respirator by being rotated about an axis parallel to the first and second lines of demarcation.

* * * * *